United States Patent
Zavislan

(12) 
(10) Patent No.: US 6,413,252 B1
(45) Date of Patent: Jul. 2, 2002

(54) CONFOCAL MICROSCOPE FOR FACILITATING CRYOSURGERY OF TISSUE

(75) Inventor: James M. Zavislan, Pittsford, NY (US)

(73) Assignee: Lucid, Inc., Rochester, NY (US)

( * ) Notice: Subject to any disclaimer, the term of this patent is extended or adjusted under 35 U.S.C. 154(b) by 0 days.

(21) Appl. No.: 09/256,145

(22) Filed: Feb. 24, 1999

Related U.S. Application Data

(60) Provisional application No. 60/076,020, filed on Feb. 26, 1998.

(51) Int. Cl.[7] .............................................. A61B 18/18
(52) U.S. Cl. ........................ 606/22; 359/398; 359/375; 606/1
(58) Field of Search ................................ 606/1, 20–26; 359/368, 375–377, 395, 398

(56) References Cited

U.S. PATENT DOCUMENTS

| | | | |
|---|---|---|---|
| 4,663,944 A | | 5/1987 | Bernius et al. |
| 4,965,441 A | | 10/1990 | Picard |
| 5,034,613 A | | 7/1991 | Denk et al. |
| 5,070,935 A | * | 12/1991 | Sitte et al. .................... 165/61 |
| 5,120,953 A | | 6/1992 | Harris |

(List continued on next page.)

FOREIGN PATENT DOCUMENTS

| | | | |
|---|---|---|---|
| DE | 2906153 | * | 9/1980 |
| JP | 63263440 | * | 10/1988 |
| WO | WO 96/21938 | | 7/1996 |

OTHER PUBLICATIONS

"Candela Dynamic Cooling Device" at www.cizr.com/PROD.DCD.html, printed Feb. 23, 1999.

Milind Rajadhyaksha, Melanie Grossman, Dina Esterowitz, Robert H. Webb, and R. Rox Anderson, In Vivo Confocal Scanning Laser Microscopy of Human Skin: Melanin Provides Strong Contrast, Confocal Scanning Laser Microscopy, vol. 104, No. 6, pp. 1–7, Jun. 1995.

Milind Rajadhyasha and James M. Zavislan, Confocal laser microscope images tissue in vivo, Laser Focus World, vol. 33, No. 2, pp. 119–127, Feb. 1997.

Joseph M. Schmitt, Alex Knuttel, Amir Gandjbakhche and Robert F. Bonner, Optical characterization of dense tissues using low–coherence interferometry, SPIE vol. 1889, pp. 197–211, 1993.

Primary Examiner—Michael Peffley
(74) Attorney, Agent, or Firm—Kenneth J. Lukacher

(57) ABSTRACT

A confocal microscope is provided including a confocal imaging system having an objective lens, and a device which can be an attachment to the confocal imaging system, or a part thereof. The device has a housing with an interior cavity and two opposite ends, where one end of the housing receives the objective lens, and at the other end of the housing which is attached to, or is a part of, the housing which forms that other end. The chamber has first and second plates presenting two opposing sides of the chamber, where the first plate lies adjacent the tissue to be treated, and the second plate is attached to the housing. The interior cavity of the housing has a window defining a first volume between the window and the objective lens, and a second volume between the window and the chamber. The first volume has an immersion liquid optically matched to the objective lens, and the second volume is approximately evacuated. The confocal imaging system, via the device, focuses light into the tissue and collects returned light from the tissue to produce images representing one or more sections of the tissue. To freeze the tissue, the chamber receives a cryogenic fluid, such as liquid nitrogen, thereby cryosurgically treating the tissue below the chamber which includes the imaged tissue. The chamber has an input port to receive the cryogenic fluid and an output port to vent the cryogenic fluid. The confocal microscope can provide images of the tissue before, during and after cryosurgical treatment.

34 Claims, 1 Drawing Sheet

U.S. PATENT DOCUMENTS

| | | |
|---|---|---|
| 5,122,653 A | 6/1992 | Ohki |
| 5,257,128 A | 10/1993 | Diller et al. |
| 5,486,172 A * | 1/1996 | Chess .......................... 606/20 |
| 5,532,874 A | 7/1996 | Stein |
| 5,598,888 A | 2/1997 | Sullivan et al. |
| 5,632,741 A | 5/1997 | Zavislan et al. |
| 5,653,706 A | 8/1997 | Zavislan et al. |
| 5,654,546 A * | 8/1997 | Lindsay ..................... 250/306 |
| 5,719,700 A | 2/1998 | Corcuff et al. |
| 5,750,989 A | 5/1998 | Lindsay et al. |
| 5,788,639 A | 8/1998 | Zavislan et al. |
| 5,880,880 A | 3/1999 | Anderson et al. |
| 5,906,636 A * | 5/1999 | Casscells, III et al. ....... 607/96 |
| 5,995,867 A * | 11/1999 | Zavislan ..................... 600/476 |
| 6,162,210 A * | 12/2000 | Shadduck ...................... 606/5 |
| 6,162,211 A * | 12/2000 | Tankovich et al. ............. 606/9 |

* cited by examiner

CONFOCAL MICROSCOPE FOR FACILITATING CRYOSURGERY OF TISSUE

This application claims the benefit of priority to U.S. Provisional Application Ser. No. 60/076,020, filed Feb. 26, 1998.

FIELD OF THE INVENTION

The present invention relates to a confocal microscope (apparatus, method, and system) for in-vivo examinations of tissue, and particularly to a confocal microscope which facilitates cryosurgical treatment of tissue being imaged by the microscope. This invention is especially suitable for providing an instrument to examine tissue having a lesion to be treated, to cryosurgically treat the lesion, and then to examine the tissue to evaluate the effectiveness of such treatment. The term tissue herein refers to naturally or surgically exposed tissue, and the term lesion refers to an abnormality in the tissue or diseased tissue.

BACKGROUND OF THE INVENTION

Confocal microscopes for scanning tissue can produce microscopic images of tissue sections. Such microscopic image sections may be made in-vivo in tissue without requiring a biopsy specimen of a lesion in the tissue. An example of a confocal microscope is the "Vivascope" manufactured by Lucid Technologies, Inc. of Henrietta, New York. Other examples of confocal microscopes are found in U.S. Pat. No. 5,788,639 and Published International Application WO96/21938. Confocal scanning microscopes are also described in Milind Rajadhyaksha et al., "In vivo Confocal Scanning Laser Microscopy of Human Skin: Melanin provides strong contrast," The Journal of Investigative Dermatology, Volume 104, No. 6, June 1995, pages 1–7, and Milind Rajadhyaksha et al., "Confocal laser microscope images tissue in vivo," Laser Focus World, February 1997, pages 119–127. These confocal microscopes have confocal optics which direct light to the patient's tissue and image the returned light. Although these confocal microscopes are useful for examination of lesions or other diseased tissue, they have no capability for facilitating cryosurgical treatment of imaged tissue. Cryosurgery involves the freezing of tissue, such as performed for treating dermal lesions, for example, lentigos (freckles), or papillomas (warts).

SUMMARY OF THE INVENTION

Accordingly, the principal object of the present invention is to provide an improved confocal microscope system which facilitates cryosurgical treatment of the tissue being imaged by the microscope.

Another object of the present invention is to provide an improved system by which a physician can confocally image tissue to assure that a lesion in the tissue is cryosurgically treated, while minimizing the damage to healthy tissue around the lesion.

Briefly described, the present invention embodies a confocal microscope for imaging tissue having a confocal imaging system with an objective lens. The tissue may represent in-vivo tissue having a lesion to be cryosurgically treated. A device for cryosurgery while viewing the tissue, via the confocal imaging system of the microscope, includes a housing with an interior cavity and two opposite ends. The objective lens is received in the interior cavity at one end of the housing. At the other end of the housing, the housing forms, or has attached thereto, a chamber which can lie adjacent to the tissue. The confocal imaging system focuses light into the tissue, and collects returned light from the tissue via the housing, to produce an image of the tissue representing a section of the tissue. A cryogenic fluid, such as liquid nitrogen, is supplied to the chamber, thereby enabling cryosurgically treatment of the imaged tissue to be carried out.

The interior cavity of the housing may have a window defining a first volume between the window and the objective lens, and a second volume between the window and the chamber. The first volume has an immersion liquid optically matched to the objective lens, and the second volume is approximately evacuated to form a vacuum or a partial vacuum.

The chamber further has an input port to receive the cryogenic fluid and an output port to vent the cryogenic fluid. A source of the cryogenic fluid is piped through a control value to the input port of the chamber to effect cryosurgical treatment of the imaged tissue.

The confocal microscope enables imaging of the tissue before, during and after cryosurgical treatment of the imaged tissue. Boundaries of a lesion in the tissue to be treated may thus be located in images of the tissue before treatment, and then during and after treatment, images of the same tissue may be viewed to determine the effect of the treatment of the lesion.

The present invention also embodies a method for confocally imaging tissue and facilitating cryosurgery of the tissue including the steps of: providing a housing having an interior cavity and one end coupled to the objective lens of a confocal microscope, providing a chamber coupled to the other end of the housing, supplying a cryogenic fluid to the chamber to freeze the tissue, projecting a beam through the interior cavity and the chamber into the tissue and collecting returned light from the tissue with the aid of the confocal microscope to produce signals representing an image of a section of the tissue, and providing a display of the section in accordance with the signals.

In addition, the present invention provides a system for imaging tissue including a confocal imaging system which provides images of one or more sections of in-vivo tissue, and a chamber adjacent to the tissue and coupled to the confocal imaging system through which fluid may be supplied to effect a temperature variation in the imaged tissue during imaging.

Although the present invention is described to provide cryosurgery, other fluids than a cryogenic fluid may be supplied to the chamber to effect other temperature variation of the tissue being imaged, such as a hot fluid to thaw the tissue or cause thermolysis of tissue.

BRIEF DESCRIPTION OF THE DRAWING

The foregoing objects, features and advantages of the invention will become more apparent from a reading of the following description in connection with the accompanying drawings, in which.

DETAILED DESCRIPTION OF THE INVENTION

Figure 1:
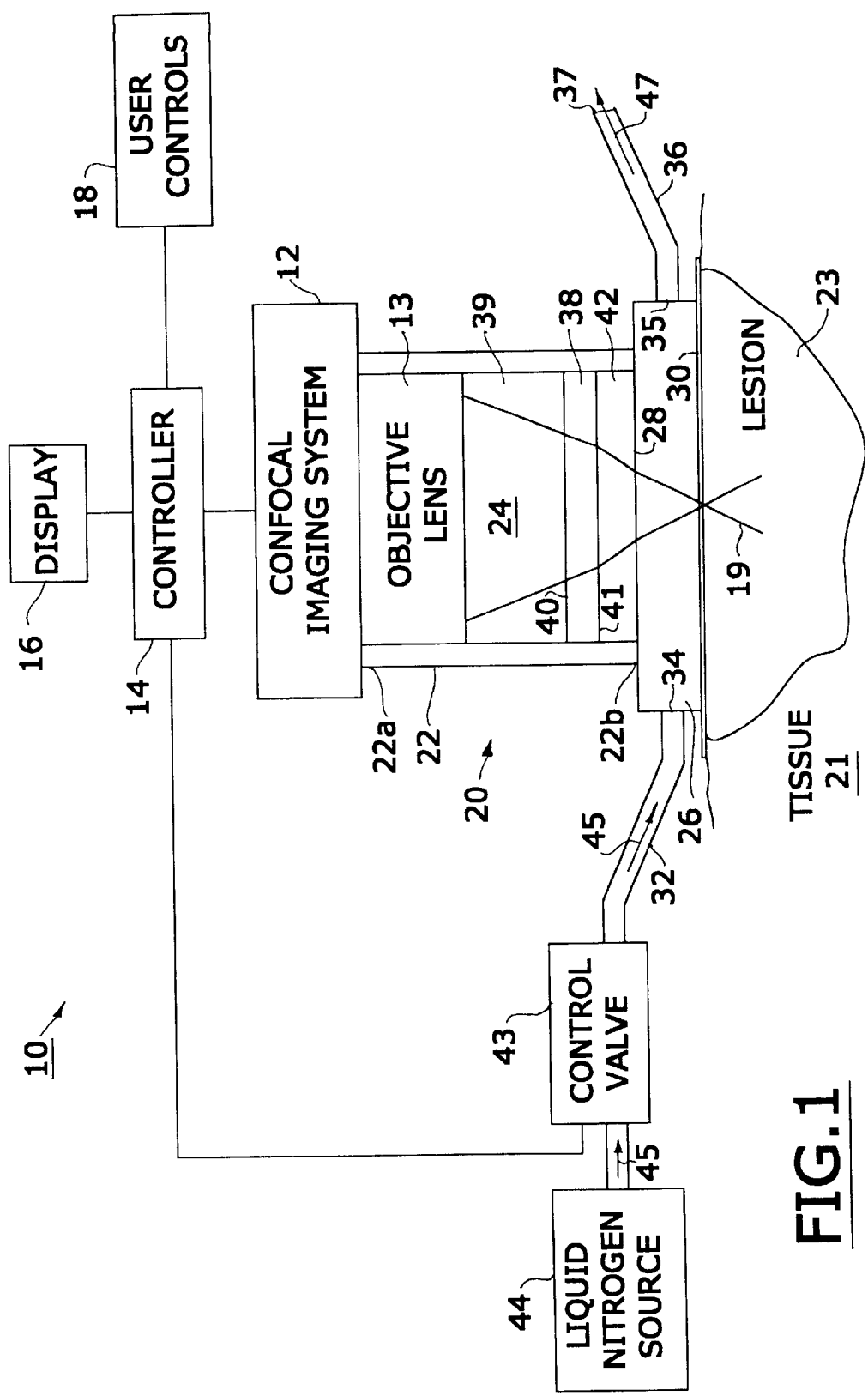
FIG. 1 is a block diagram of the confocal microscope in accordance with the present invention.

Referring to FIG. 1, a confocal microscope 10 is shown having a confocal imaging system 12 with an objective lens 13. The confocal imaging system may be the same as described in U.S. Pat. No. 5,788,639, or as described in Published International Application WO96/21938, which are both herein incorporated by reference. The confocal imaging system 12 may further comprise a controller 14, a display 16, and user controls 18, or these may be components separate from system 12. An example of confocal imaging system 12 including such components is the "Vivascope" manufactured by Lucid Technologies, Inc. of Henrietta, N.Y. Since the details of the confocal imaging system is discussed in theses references, a full explanation of the system is not provided herein.

The confocal imaging system 12 (often referred to as a head) has a laser source for producing a beam 19 and optics (not shown) for scanning the beam (a raster scan may be used). The beam is focused with objective lens 13 at a scanning plane on the surface of the tissue or inside the tissue 21. The return light from the tissue is collected by objective lens 13 and confocally detected and converted into electrical signals, representing a section of the tissue, to controller 14. Controller 14 sends such signals to display 16 coupled to the controller. The controller may be a computer, such as a PC, which uses typical display driving software for producing images on display 16. For example, controller 14 may sample the signal representing the tissue from the imaging system to acquire data which represent successive raster lines of an image correlated to successive scans of the imaging beam rough the tissue or on the surface thereof. The scan position of the beam may further be provided to controller 14. Although reference is made hereinafter to a confocal imaging system 12 in system 10, other types of imaging systems which provides images of sections of tissue may also be used, such as systems based on optical coherence tomography, such as described in Schmitt et al., "Optical characterization of disease tissues using low-coherence interferometry," Proc. of SPIE, Volume 1889 (1993), or a two-photon microscope, such as described in U.S. Pat. No. 5,034,613 to Denk et al.

The confocal microscope 10 further includes a device shown as an attachment 20 in the figure. Although described herein as an attachment, the device may be an integrated assembly with confocal imaging system 12. Attachment 20 has a housing 22, which may be cylindrical in shape, having an interior cavity 24. Housing 22 has two opposite ends 22a and 22b in which objective lens 13 is received in interior cavity 24 at end 22a. Housing 22 may be mechanically coupled to objective lens 13 by screws (not shown), or may be an integrated part of the confocal imaging system 12. Attachment 20 also includes a hollow chamber 26 having a first plate 28 and a second plate 30 at two opposing sides of the chamber. Plates 28 and 30 may be approximately parallel to each other. Plate 30 lies adjacent the tissue 21 to be imaged, while plate 28 is coupled to end 22b of housing 22. Spacers, such as glass or metal, may be provided between the plates 28 and 30 to define the other sides of the chamber 26. Chamber 26 may be coupled to housing 22 by means of screws (not shown), or chamber 26 may be a part of the housing forming end 22b. Plate 30, or each of plates 28 and 30, may be a sapphire substrate. Plate 30 may be made of other material, so long as the material is transmissive to the imaging beam of the confocal imaging system and has high thermal conductivity. Plates 28 and 30 may be made of dissimilar materials which are transmissive to the imaging beam, however, they must be thermo-mechanically compatible, for example, in terms of thermal expansion. Chamber 26 may represent a hollow cell between the housing 22 and the tissue 21 to be imaged by confocal imaging system 12. Tissue 21 may be in-vivo, such as that of a patient, and may be dermal or internal tissue of the patent's body having a lesion 23 to be treated. For example, where tissue 21 represents dermal tissue, lesion 23 may represent lentigo (freckles), or papilloma (warts).

Interior cavity 24 of housing 22 contains a window 38 between objective lens 13 and plate 28 of chamber 26. The window 38 defines a first volume 39 between the window (i.e., surface 40 of the window) and end 22a of the housing, and a second volume 42 between the window (i.e., surface 41 of the window) and chamber 26. For example, the window may be glass, or other rigid material transmissive to beam 19. In the first volume 39 is an immersion fluid which provides optical index matching of the objective lens 13 to window 38. First volume 39 may be filled with the immersion fluid from a reservoir (not shown) external of the housing 22. The second volume 42 is approximately evacuated to form a vacuum or partial vacuum. The vacuum may be permanent or periodically evacuated from a valve (not shown) on the housing. Optical aberrations of the objective lens 13 may be balanced to account for the optical thickness of plates 28 and 30, and window 38.

A cryogenic fluid, such as liquid nitrogen, may be supplied to chamber 26, via piping 32 to an opening (or input port) 34 in the chamber, and vented (at vent 37) from chamber 26, via piping 36 from an opening (or output port) 35 to the chamber. A control valve 43 controls the amount (or rate) of the liquid nitrogen flowing from a liquid nitrogen source 44, such as a tank, to chamber 26 via piping 32. The position of control valve 43 may be set via electrical signals from controller 14, or control valve 43 may be a manually operated mechanical valve. The liquid nitrogen provided to chamber 26 between plates 28 and 30 freezes tissue 21 under plate 30, and thus lesion 23 in the tissue. Cryogenic fluids other than liquid nitrogen may also be used, so long as they are transparent to the beam (or radiation) of the confocal imaging system and can generate a sufficiently low temperature at plate 30 to freeze lesion 23. Window 38 and vacuum 42 provide insulating layers which prevents immersion fluid in first volume 39 from freezing when liquid nitrogen is provided to chamber 26. The housing may be an insulating housing in which its outer wall can further provide insulation of the immersion fluid from freezing. For example, the housing may be composed of plastic, or other insulating material.

The scanning imaging beam 19 provided by confocal imaging system 12 is focused by objective lens 13 through attachment 20 on the surface of the tissue or into the tissue 21, i.e., the beam is transmitted through the immersion fluid in first volume 39, window 38, vacuum 42, and plates 28 and 30 of chamber 26. An example of imaging beam 19 is shown in the figure. Returned light is transmitted in the reverse direction through attachment 20 to objective lens 13 of the confocal imaging system 12.

Confocal microscope 10 can be used to cryosurgically treat a lesion 23 in tissue 21. A physician, or other operator, positions the attachment 20 of the confocal microscope over the area of the tissue which has a lesion to be treated. The physician can then confocally image the tissue through the attachment 20 using the confocal imaging system 12 to provide images of one or more sections of the tissue on display 16. Using user controls 18, the physician can direct the confocal imaging system 12 to image the tissue 19 at particular depths below its surface. User controls 18 may be any typical user interface device, such as a keyboard, mouse, or joystick. In this manner the physician can determine if the lesion is in the field of view of the confocal imaging system and hence below chamber 26, and can further assess the boundaries (or margins) of the lesion 23 being imaged. If the lesion 23 is not properly being imaged, the physician may relocate confocal microscope 10 until the lesion is viewed in the image on display 16.

With the lesion 23 being imaged by the confocal imaging system 12, the physician directs the controller 14, via user controls 18, to set control valve 43 to a position which releases liquid nitrogen from liquid nitrogen source 44 to chamber 26. The flow of the liquid nitrogen is indicated by the arrow 45 in the figure, and venting of the liquid nitrogen by the arrow 47. The liquid nitrogen reduces the temperature of chamber 26 to chill plate 30, which causes the lesion below plate 30 to freeze, thereby destroying the cells (lysis) associated with the lesion. In other words, the temperature variation of the chamber 26 is applied to the tissue 21 via plate 30. The physician can monitor the cryosurgical treatment in real-time by viewing images of one or more tissue sections on display 16. When treatment is complete, the control valve 43 is set to stop the flow of liquid nitrogen to chamber 26. The physician can then image the treated tissue with the confocal imaging system to determine the effectiveness of the cryosurgical treatment. The above process may be repeated if further treatment of the lesion is necessary. Also, if the size of the lesion is greater than the field of view of the confocal imaging system or the extent of chamber 26 coverage of the tissue surface, the physician may need to relocate confocal microscope 10 to further treat the lesion.

The confocal microscope 10 thus facilitates cryosurgical treatment of tissue, such as a lesion, and further allows a physician to assure that a lesion is cryosurgically treated by viewing the effectiveness of treatment. The confocal microscope also allows a physician to locate the boundaries of the area of tissue having the lesion to be cryosurgically treated, thereby minimizing the risk of damage to healthy tissue around the lesion.

The confocal microscope 10 may also be used to treat tissue using heat by supplying hot fluids, such as hot liquid, to chamber 26. This may be achieved by replacing the liquid nitrogen source 44 with a hot fluid source, or by using two alternative sources (a nitrogen source and a hot fluid source) which can be passed by control valve 43 (under control by controller 14) through piping 32 to chamber 26. Treatment of lesion 23 by heat can provide thermolysis of lesion cells, or can be used after cryosurgical treatment of a lesion to observe the lesion as it thaws in response to applied heat. Confocal microscope 10 thus may provide imaging of one or more sections of tissue before, during, and after treatment, where treatment can be by either heat or cold applied to tissue via chamber 26.

From the foregoing description, it will be apparent that there has been provided an improved confocal microscope which facilitates cryosurgery of tissue to treat lesions. Variations and modifications in the herein described confocal microscope in accordance with the invention will undoubtedly suggest themselves to those skilled in the art. Accordingly, the foregoing description should be taken as illustrative and not in a limiting sense.

What is claimed is:

1. A system for imaging tissue comprising:
   means for imaging in-vivo tissue of a patient to provide images of one or more sections of said tissue; and
   means operative by a fluid, adapted to be adjacent to said tissue and coupled to said imaging means, for effecting the temperature of said imaged tissue during imaging by said imaging means.
2. The system according to claim 1 wherein said imaging means is a confocal imaging system.
3. The system according to claim 1 wherein said imaging means is operative by optical coherence tomography.
4. The system according to claim 1 wherein said imaging means is a two-photon laser microscope.
5. A system for cryosurgically treated tissue comprising:
   means for viewing at least one section of said tissue capable of being below the surface of said tissue to locate a lesion in said tissue in or on patient's body; and
   means for cryosurgically treating said lesion in said tissue while minimizing damage to other tissue about said lesion.
6. The system according to claim 5 wherein said cryosurgically treating means comprises a chamber having a surface adjacent the tissue having said lesion.
7. The system according to claim 6 wherein said cryosurgically treating means further comprises means coupled to said chamber for reducing the temperature of said surface to perform cryosurgery of the tissue adjacent said surface.
8. The system according to claim 7 wherein said viewing means is coupled to said chamber to enable viewing of said tissue through said surface, and said viewing means further comprises a housing having at least one insulating means therein to insulate against the reduction of temperature which performs cryosurgery of the tissue adjacent said surface.
9. A confocal microscope for facilitating cryosurgery of tissue comprising:
   a confocal imaging system having an objective lens;
   cryogenically operative means comprising a housing with an interior cavity and two opposite ends in which said objective lens is received in said interior cavity at one of said ends, and a chamber at the other end of said housing which can lie adjacent to said tissue, wherein said tissue represents in-vivo tissue of a patient;
   said confocal imaging system is adapted to focus light into said tissue and collects light from said tissue through said chamber to produce an image of said tissue representing at least one section of said tissue; and
   means coupled to said cryogenically operative means for supplying a cryogenic fluid to said chamber to cryosurgically treat said tissue imaged by said confocal imaging system.
10. The confocal microscope according to claim 9 wherein said chamber comprises two approximately parallel plates, in which one of said plates lies adjacent said tissue.
11. The confocal microscope according to claim 10 wherein at least one of said plates is composed of sapphire.
12. A confocal microscope for facilitating cryosurgery of tissue comprising:
   a confocal imaging system having an objective lens;
   cryogenically operative means comprising a housing with an interior cavity and two opposite ends in which said objective lens is received in said interior cavity at one of said ends, and a chamber at the other end of said housing which can lie adjacent to said tissue;
   said confocal imaging system is adapted to focus light into said tissue and collects light from said tissue through said chamber to produce an image of said tissue representing at least one section of said tissue; and
   means coupled to said cryogenically operative means for supplying a cryogenic fluid to said chamber to cryosurgically treat said tissue imaged by said confocal imaging system, wherein said housing has a window in said interior cavity defining a first volume between said window and said objective lens, and a second volume between said window and said chamber.

13. The confocal microscope according to claim 12 wherein said first volume has a fluid optically index matched to said objective lens.

14. The confocal microscope according to claim 12 wherein said second volume is approximately evacuated.

15. The confocal microscope according to claim 9 wherein said means coupled to said cryogenically operative means comprises a source of cryogenic fluid, a control valve coupled to said source to control the supply of said cryogenic fluid to said chamber, and means through which said fluid from said control valve is received in said chamber.

16. The confocal microscope according to claim 15 wherein said means coupled to said cryogenically operative means further comprises means for venting said cryogenic fluid from said chamber.

17. The confocal microscope according to claim 9 wherein said cryogenic fluid is liquid nitrogen.

18. A confocal microscope for facilitating cryosurgery of tissue comprising:
    a confocal imaging system having an objective lens;
    cryogenically operative means comprising a housing with an interior cavity and two opposite ends in which said objective lens is received in said interior cavity at one of said ends, and a chamber at the other end of said housing which can lie adjacent to said tissue;
    said confocal imaging system is adapted to focus light into said tissue and collects light from said tissue through said chamber to produce an image of said tissue representing at least one section of said tissue;
    means coupled to said cryogenically operative means for supplying a cryogenic fluid to said chamber to cryosurgically treat said tissue imaged by said confocal imaging system; and
    means coupled to said cryogenically operative means for supplying another fluid to said chamber to treat said tissue being imaged by said confocal imaging system.

19. The confocal microscope according to claim 18 wherein said another fluid represents a hot fluid.

20. The confocal microscope according to claim 9 wherein said chamber further comprises an input port to receive the cryogenic fluid and an output port to vent the cryogenic fluid.

21. The confocal microscope according to claim 9 wherein said confocal imaging system is adapted to focus light into a lesion located in healthy tissue providing said in-vivo tissue.

22. The confocal microscope according to claim 21 wherein said cryogenic fluid is supplied to said chamber of said cryogenically operative means when at least said lesion is being imaged by said confocal imaging system to minimize damage to said healthy tissue.

23. The confocal microscope according to claim 9 wherein said chamber has at least one exterior surface capable of lying on the surface of said tissue to enable application of temperature variation to said tissue when said cryogenic fluid is supplied to said chamber.

24. A method for confocally imaging tissue and facilitating cryosurgery of said tissue comprising the steps of:
    providing a housing having an interior cavity and one end coupled to the objective lens of a confocal microscope;
    providing a chamber coupled to the other end of said housing;
    projecting a beam through said interior cavity and said chamber into said tissue and collecting returned light from said tissue with the aid of said confocal microscope to produce signals representing an image of a section of said tissue;
    providing a display of said section in accordance with said signals representing an image of a section of said tissue;
    locating said confocal microscope to provide in said image on said display the part of the tissue where cryosurgery is to be performed; and
    supplying a cryogenic fluid to said chamber to perform cryosurgery of at least the located tissue in said image while minimizing damage to other tissue about said located tissue.

25. The method according to claim 24 further comprises:
    viewing on said display an image of a lesion in said tissue to be cryosurgical treated before said supplying step is carried out;
    viewing on said display an image of said lesion while said supplying step is carried out; and
    viewing on said display an image of said lesion to determine the effect of said cryosurgical treatment to said lesion after said supplying step is carried out.

26. The method according to claim 24 further comprising the step of locating on said display of an imaged tissue a lesion to be treated.

27. The method according to claim 24 further comprising the step of repeating said locating and supplying steps at another part of said tissue to perform cryosurgery at multiple locations of said tissue.

28. An attachment for a microscope for imaging tissue having an objective lens facing the tissue comprising:
    a housing having an interior cavity and two opposite ends in which said objective lens is adapted to be received in said interior cavity at one of said ends;
    a chamber having first and second plates representing two opposing sides of said chamber, in which said first plate has a surface capable of lying upon said tissue and a second plate is coupled to the other one of said ends of said housing; and
    means for supplying a fluid to said chamber to effect temperature variation to said tissue.

29. The attachment according to claim 28 wherein said housing further comprises a window between said objective lens and said chamber to define a first volume in said housing between said window and said one end of said housing when said objective lens is received in said interior cavity of said housing, and a second volume in said housing between said window and said chamber, in which an index matching fluid is provided in said first volume, and said second volume is approximately evacuated.

30. The attachment according to claim 29 wherein said fluid is a cryogenic fluid, and said window and said evaluated second volume insulates said index matching fluid from freezing when said cryogenic fluid is provided to said chamber.

31. The attachment according to claim 28 wherein said fluid is one of a cryogenic fluid and a hot fluid.

32. The attachment according to claim 28 wherein said means further comprises:
    a source for said fluid;
    means coupled to said source and said chamber for controlling the amount of said fluid provided to said chamber; and
    a vent coupled to said chamber.

33. The attachment according to claim 28 wherein at one or said first and second plates is composed of sapphire.

34. The attachment according to claim 28 wherein said liquid is liquid nitrogen.

* * * * *